US007326730B2

(12) United States Patent
Wang et al.

(10) Patent No.: US 7,326,730 B2
(45) Date of Patent: Feb. 5, 2008

(54) AMINOADAMANTANE DERIVATIVES AS THERAPEUTIC AGENTS

(75) Inventors: Yuqiang Wang, Mountain View, CA (US); Wenqing Ye, Fremont, CA (US); James W. Larrick, Woodside, CA (US); Jonathan S. Stemler, Chapel Hill, NC (US); Stuart A. Lipton, Rancho Santa Fe, CA (US)

(73) Assignee: Adamas Pharmaceuticals, Inc., Emeryville, CA (US)

( * ) Notice: Subject to any disclaimer, the term of this patent is extended or adjusted under 35 U.S.C. 154(b) by 0 days.

(21) Appl. No.: 11/283,241

(22) Filed: Nov. 17, 2005

(65) Prior Publication Data

US 2006/0106222 A1    May 18, 2006

Related U.S. Application Data

(63) Continuation of application No. 10/634,069, filed on Aug. 4, 2003, now abandoned, which is a continuation of application No. 10/199,156, filed on Jul. 19, 2002, now Pat. No. 6,620,845, which is a continuation of application No. 09/510,099, filed on Feb. 22, 2000, now Pat. No. 6,444,702.

(51) Int. Cl.
*A01N 37/00* (2006.01)
(52) U.S. Cl. .................. 514/511; 514/617; 514/619
(58) Field of Classification Search ................ 514/511, 514/617, 619
See application file for complete search history.

(56) References Cited

U.S. PATENT DOCUMENTS

| | | | |
|---|---|---|---|
| 3,328,251 A | 6/1967 | Smith ........................ 167/65 |
| 3,391,142 A | 7/1968 | Mills et al. ................. 260/268 |
| 4,122,193 A | 10/1978 | Scherm et al. ............. 424/330 |
| 4,346,112 A | 8/1982 | Henkel et al. ............. 424/325 |
| 4,351,847 A | 9/1982 | Griffith et al. ............. 424/325 |
| 5,053,419 A | 10/1991 | Lipton ....................... 514/356 |
| 5,061,703 A | 10/1991 | Bormann et al. ........... 514/212 |
| 5,091,391 A | 2/1992 | Aizenman et al. ......... 514/311 |
| 5,234,956 A | 8/1993 | Lipton ....................... 514/724 |
| 5,334,618 A | 8/1994 | Lipton ....................... 514/659 |
| 5,382,601 A | 1/1995 | Nürnberg et al. ........... 514/775 |
| 5,455,279 A | 10/1995 | Lipton ....................... 514/742 |
| 5,506,231 A | 4/1996 | Lipton ....................... 514/289 |
| 5,614,560 A | 3/1997 | Lipton ....................... 514/659 |
| 5,677,349 A | 10/1997 | Gilad et al. ................. 514/634 |
| 5,747,545 A | 5/1998 | Lipton ....................... 514/742 |
| 5,776,935 A | 7/1998 | Danysz et al. ............. 514/248 |
| 5,801,203 A | 9/1998 | Lipton ....................... 514/742 |
| 5,922,773 A | 7/1999 | Lipton et al. ............... 514/649 |
| 6,034,134 A | 3/2000 | Gold et al. ................. 514/579 |
| 6,046,232 A | 4/2000 | Kelleher et al. ........... 514/464 |
| 6,057,364 A | 5/2000 | Jasys et al. ................. 514/511 |
| 6,066,652 A | 5/2000 | Zenner et al. ............. 514/317 |
| 6,071,876 A | 6/2000 | Lipton et al. ................... 514/3 |
| 6,071,966 A | 6/2000 | Gold et al. ................. 514/579 |
| 6,114,392 A | 9/2000 | Gilad et al. ................. 514/634 |
| 6,172,116 B1 | 1/2001 | Elstner ....................... 514/579 |
| 6,218,404 B1 | 4/2001 | Bigge et al. ................. 514/317 |
| 6,255,348 B1 | 7/2001 | Elstner ....................... 514/579 |
| 6,344,590 B1 | 2/2002 | Nakano et al. ............. 568/591 |
| 6,392,104 B1 | 5/2002 | Ishii et al. ................. 568/818 |
| 6,429,314 B1 | 8/2002 | Ishii et al. ................. 546/112 |
| 6,444,702 B1 * | 9/2002 | Wang et al. ................. 514/511 |
| 6,468,487 B1 | 10/2002 | Ishii et al. ................ 423/239.1 |
| 6,482,854 B1 | 11/2002 | Lipton et al. ............... 514/523 |
| 6,500,866 B1 | 12/2002 | Gillespie et al. ............ 514/631 |

(Continued)

FOREIGN PATENT DOCUMENTS

| | | |
|---|---|---|
| EP | 0 392 059 A1 | 10/1990 |
| EP | 0 870 757 A2 | 10/1998 |
| EP | 0 927 711 A1 | 7/1999 |
| GB | 1 173 492 | 12/1969 |

(Continued)

OTHER PUBLICATIONS

Bachurin et al. *Annals of the New York Academy of Science*, 939:219-236 (2001).
Green *Protective Groups in Organic Synthesis*, John Wiley & Sons, pp. 70-71 (1981).
Harkany et al. *Eur. J. Neurosci.*, 12:2735-2745 (2000).
Jain *Exp. Op. Invest. Drugs*, 9(6):1-10 (2000).
Koch et al. *J. Am. Chem. Soc.*, 95(26):8631-8637 (1973).

(Continued)

*Primary Examiner*—Yvonne Eyler
*Assistant Examiner*—Sudhakar Katakam
(74) *Attorney, Agent, or Firm*—Ivor R. Elrifi; David K. Johnson; Mintz, Levin, Cohn, Ferris, Glovsky and Popeo, P.C.

(57) ABSTRACT

The present invention provides novel aminoadamantane derivatives, methods of making the derivatives, compositions including the novel aminoadamantane derivatives, and methods for the treatment and prevention of neurological diseases using the derivatives and compositions There are a variety of neurological disorders that can be treated using the present invention, including, for example, the following: neurological disorders arising from trauma, ischemic or hypoxic conditions that can be treated include stroke, hypoglycemia, cerebral ischemia, cardiac arrest, spinal cord trauma, head trauma, perinatal hypoxia, cardiac arrest and hypoglycemic neuronal damage; neurodegenerative disorders such as epilepsy, Alzheimer's disease, Huntington's disease Parkinsonism, and amyotrophic lateral sclerosis; other diseases or disorders such as convulsion, pain, depression, anxiety, schizophrenia, muscle spasms, migraine headaches, urinary incontinence, nicotine withdrawal, opiate tolerance and withdrawal, emesis, brain edema, tardive dyskinesia, AIDS-induced dementia, ocular damage, retinopathy, cognitive disorders, and neuronal injury associated with HIV-infection such as dysfunction in cognition, movement and sensation.

13 Claims, 6 Drawing Sheets

U.S. PATENT DOCUMENTS

| | | |
|---|---|---|
| 6,503,947 B1 | 1/2003 | Lipton et al. ............... 514/575 |
| 6,525,017 B1 | 2/2003 | Lipton ........................... 514/2 |
| 6,602,862 B1 | 8/2003 | Kelly et al. ................ 514/183 |
| 6,620,845 B2 | 9/2003 | Wang et al. ................ 514/511 |
| 6,717,012 B2 | 4/2004 | Wang et al. ................ 564/299 |
| 2003/0045574 A1 | 3/2003 | Wang et al. ................ 514/484 |
| 2003/0130354 A1 | 7/2003 | Gillespie et al. ............ 514/632 |
| 2003/0144319 A1 | 7/2003 | Bigge et al. ................ 514/307 |
| 2004/0009613 A1 | 1/2004 | Zhou et al. ................ 436/518 |
| 2004/0029929 A1 | 2/2004 | Wang et al. ................ 514/351 |
| 2004/0043378 A1 | 3/2004 | Zhou et al. ..................... 435/5 |
| 2004/0122090 A1 | 6/2004 | Lipton ........................ 514/510 |
| 2004/0186320 A1 | 9/2004 | Wang et al. ................ 564/299 |

FOREIGN PATENT DOCUMENTS

| | | |
|---|---|---|
| JP | 58-4718 | 1/1983 |
| JP | 06161125 | 6/1994 |
| JP | 11302211 A2 | 11/1999 |
| JP | 2003137841 A2 | 5/2003 |
| JP | 2003137842 A2 | 5/2003 |
| WO | WO 99/31051 | 6/1999 |
| WO | WO 01/62706 A1 | 8/2001 |
| WO | WO 02/45710 A1 | 6/2002 |
| WO | WO 02/078615 A2 | 10/2002 |

OTHER PUBLICATIONS

Kotani et al. *Chem. Pharmac. Bull.*, 33(11):4680-4684 (1985.
Makarova et al. *Russian J. Gen. Chem.*, 70(5):758-760; translated from *Zhurnal Obshchei Khimii*, 70(5):812-814 (2000).
Mella et al. *J. Org. Chem.*, 61(4):1413-1422 (1996).
Parks et al. *J. Neurochem.*, 76:1050-1056 (2001).
Parsons et al. *Neuropharmacol.*, 38:735-767 (1999).
Wenk et al. *Life Sci.*, 66(12):1079-1083 (2000).
Klimochkin et al. *Khimiko-Farmatsevticheskii Zhurnal*, with English Abstract, 26(7-8):58-59 (1992) (Russian).
Lavrova et al. *Khimiko-Farmatsevticheskii Zhurnal*, with English Abstract, 24(1):29-31 (1990) (Russian).
Wesemann et al. *Arzneimittel-Forschung*, with English Summary, 27(7):1471-1477 (1977) (German).

* cited by examiner (a) COMPOUND 8

(b) ETHANOL (μL)

(c) METHYLENE BLUE ($10^{-5}$ M), COMPOUND 8 (M)

(d) HEMOGLOBIN, ($10^{-6}$ M), COMPOUND 8 (M)

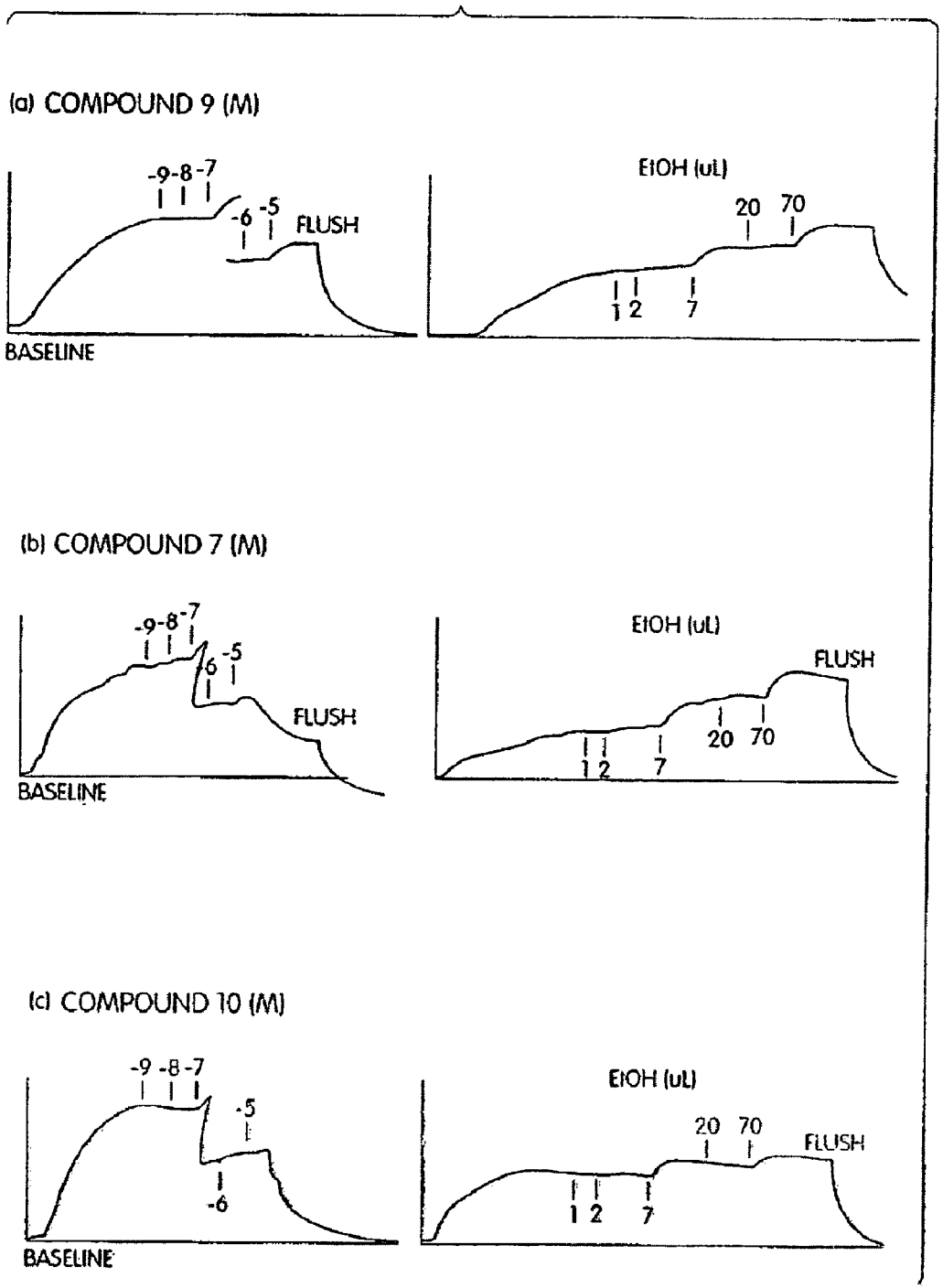

AMINOADAMANTANE DERIVATIVES AS THERAPEUTIC AGENTS

RELATED APPLICATIONS

This application is a continuation of application Ser. No. 10/634,069, filed Aug. 4, 2003 now abandoned, which is a continuation of application Ser. No. 10/199,156, filed Jul. 19, 2002, now issued as U.S. Pat. No. 6,620,845, which is a continuation of application Ser. No. 09/510,099, filed Feb. 22, 2000, now issued as U.S. Pat. No. 6,444,702. The contents of these applications are hereby incorporated by reference.

BACKGROUND OF THE INVENTION

Certain adamantane derivatives have been used to treat illnesses. Rimantadine (1-(1-aminoethyl)adamantane) is used for the prophylaxis and treatment of influenza in humans. Amantadine has been used for the treatment of both influenza and Parkinson's disease (Schwab et al., *J. Am. Med. Assoc.* (1969) 208:1168). Another derivative, memantine, is currently under clinical investigation for the treatment of various neurodegenerative diseases and has been licensed for the treatment of Parkinson's associated spasticity in Germany (Schneider et al., *Dtsch. Med. Wschr.* (1984) 109:987).

Memantine protects cortical and retinal neuron cultures from the toxicity of glutamate, NMDA and the HIV-1 coat protein gp120 (Dreyer et al., *Science* (1990) 248:364). Recent studies demonstrate that it prevents quinolinic acid-induced hippocampal damage in rats (Kelhoff and Wolf, *Eur. J. Pharmacol.* (1992) 219:451). Memantine demonstrates antiphypoxic properties in vitro and in vivo. It is thought that memantine exerts a neuroprotective effect because it is a micromolar antagonist of the NMDA receptor (Bormann J., *Eur. J. Pharmacol.* (1989) 166:591).

While memantine is being used to treat neurological disorders, the variety and severity of neurological diseases presents a need for other neuroprotective agents. The present invention provides novel compounds, compositions and methods for the treatment of neurological diseases. The present invention also provides methods of making the novel compounds.

SUMMARY OF THE INVENTION

The present invention provides compounds that can be used in the treatment of neurological diseases. The compounds are of the following formula or pharmaceutically acceptable salts thereof:

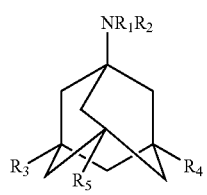

The groups $R_1$, $R_2$, $R_3$, $R_4$ and $R_5$ of the formula are independently defined. $R_1$ is H, alkyl, heteroalkyl, aryl, heteroaryl, C(O)OR$_6$ or C(O)R$_6$. $R_2$ is H, alkyl, heteroalkyl, aryl, heteroaryl, C(O)OR$_6$ or C(O)R$_6$. $R_3$ is H, alkyl, heteroalkyl, aryl or heteroaryl. $R_4$ is H, alkyl, heteroalkyl, aryl or heteroaryl. $R_5$ is OR$_7$, alkyl-OR$_7$ or heteroalkyl-OR$_7$. $R_6$ is alkyl, heteroalkyl, aryl or heteroaryl. $R_7$ is NO$_2$, C(O)R$_6$, C(O)alkyl-ONO$_2$ or C(O)heteroalkyl-ONO$_2$. The following substituents are preferred: $R_1$ and $R_2$ are H; $R_3$ and $R_4$ are H or alkyl; and, $R_7$ is NO$_2$ or C(O)alkyl-ONO$_2$.

The present invention also provides pharmaceutical compositions that can be used to treat a neurological disorder. The compositions include a pharmaceutically acceptable carrier and one or more compounds of the following formula or pharmaceutically acceptable salts thereof:

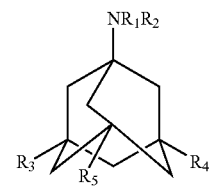

The substituents of the compounds are independently defined. $R_1$ is H, alkyl, heteroalkyl, aryl, heteroaryl, C(O)OR$_6$ or C(O)R$_6$. $R_2$ is H, alkyl, heteroalkyl, aryl, heteroaryl, C(O)OR$_6$ or C(O)R$_6$. $R_3$ is H, alkyl, heteroalkyl, aryl or heteroaryl. $R_4$ is H, alkyl, heteroalkyl, aryl or heteroaryl. $R_5$ is OR$_7$, alkyl-OR$_7$ or heteroalkyl-OR$_7$. $R_6$ is alkyl, heteroalkyl, aryl or heteroaryl. $R_7$ is NO$_2$, C(O)R$_6$, C(O)alkyl-ONO$_2$ or C(O)heteroalkyl-ONO$_2$. The following substituents are preferred: $R_1$ and $R_2$ are H; $R_3$ and $R_4$ are H or alkyl; and, $R_7$ is NO$_2$ or C(O)alkyl-ONO$_2$.

The present invention also provides methods of treating a neurological disorder. The methods include administering to a patient a pharmaceutically acceptable carrier and one or more compounds of the following formula, or pharmaceutically acceptable salts thereof:

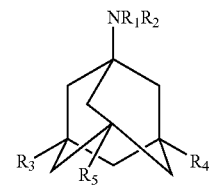

The substituents of the compounds are independently defined. $R_1$ is H, alkyl, heteroalkyl, aryl, heteroaryl, C(O)OR$_6$ or C(O)R$_6$. $R_2$ is H, alkyl, heteroalkyl, aryl, heteroaryl, C(O)OR$_6$ or C(O)R$_6$. $R_3$ is H, alkyl, heteroalkyl, aryl or heteroaryl. $R_4$ is H, alkyl, heteroalkyl, aryl or heteroaryl. $R_5$ is OR$_7$, alkyl-OR$_7$ or heteroalkyl-OR$_7$. $R_6$ is alkyl, heteroalkyl, aryl or heteroaryl. $R_7$ is NO$_2$, C(O)R$_6$, C(O)alkyl-ONO$_2$ or C(O)heteroalkyl-ONO$_2$. The following substituents are preferred: $R_1$ and $R_2$ are H; $R_3$ and $R_4$ are H or alkyl; and, $R_7$ is NO$_2$ or C(O)alkyl-ONO$_2$.

The present invention further provides methods of making compounds of the following formula or pharmaceutically acceptable salts thereof:

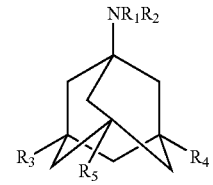

The substituents of the compounds are independently defined. $R_1$ is H, alkyl, heteroalkyl, aryl, heteroaryl, C(O)O$R_6$ or C(O)R$_6$. R$_2$ is H, alkyl, heteroalkyl, aryl, heteroaryl, C(O)OR$_6$ or C(O)R$_6$. R$_3$ is H, alkyl, heteroalkyl, aryl or heteroaryl R$_4$ is H, alkyl, heteroalkyl, aryl or heteroaryl. R$_5$ is OR$_7$, alkyl-OR$_7$ or heteroalkyl-OR$_7$. R$_6$ is alkyl, heteroalkyl, aryl or heteroaryl. R$_7$ is NO$_2$, C(O)R$_6$, C(O)alkyl-ONO$_2$ or C(O)heteroalkyl-ONO$_2$. The following substituents are preferred: R$_1$ and R$_2$ are H; R$_3$ and R$_4$ are H or alkyl; and, R$_7$ is NO$_2$ or C(O)alkyl-ONO$_2$.

Preferably, the methods involve oxidizing a compound of the following formula:

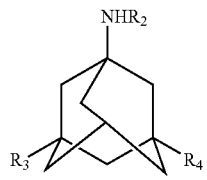

Preferably, the methods further involve nitrating a compound of the formula:

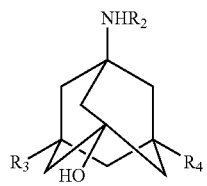

Preferably, the compound is treated with H$_2$ $_{SO4}$ and water in the oxidation step. The nitration step preferably includes treatment with HNO$_3$ and Ac$_2$O.

BRIEF DESCRIPTION OF THE DRAWINGS

FIG. 7a shows that relaxations were seen at 10$^{-8}$ M and complete relaxation was achieved at 10$^{-6}$ M. FIG. 7b shows the effect of solvent. FIG. 7c shows that relaxations were attenuated by methylene blue. FIG. 7d shows that relaxations were attenuated by hemoglobin.

FIG. 8 shows that the action of aminoadamantane derivatives are specific. Compound 9 (a) and 10 (c) produced either no effect or slight blood vessel contractions that were comparable to those produced by solvent (EtOH) alone. Compound 7 (b) produced modest relaxation at a 10 microM concentration.

DESCRIPTION OF THE SPECIFIC EMBODIMENTS

Figure 1:
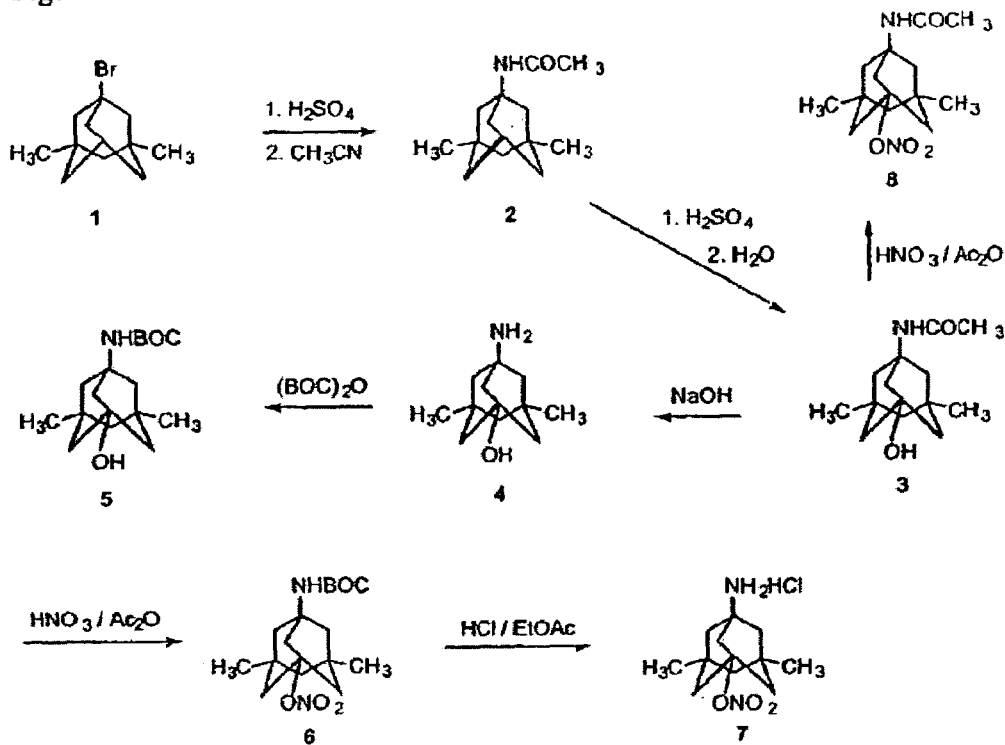
FIG. 1 shows the synthesis of an adamantane nitrate derivative.

The term "Alkyl" refers to unsubstituted or substituted linear, branched or cyclic alkyl carbon chains of up to 15 carbon atoms. Linear alkyl groups include, for example, methyl, ethyl, n-propyl, n-butyl, n-pentyl, n-hexyl, n-heptyl and n-octyl. Branched alkyl groups include, for example, iso-propyl, sec-butyl, iso-butyl, tert-butyl and neopentyl. Cyclic alkyl groups include, for example, cyclopropyl, cyclobutyl, cyclopentyl and cyclohexyl. Alkyl groups can be substituted with one or more substituents. Nonlimiting examples of such substituents include NO$_2$, ONO$_2$, F, Cl, Br, I, OH, OCH$_3$, CO$_2$H, CO$_2$CH$_3$, CN, aryl and heteroaryl. Where "alkyl" is used in a context such as "alkyl-ONO$_2$," it refers to an alkyl group that is substituted with a ONO$_2$ moiety. Where "alkyl" is used in a context such as "C(O) alkyl-ONO$_2$," it refers to an alkyl group that is connected to a carbonyl group at one position and that is substituted with a ONO$_2$ moiety.

The term "Heteroalkyl" refers to unsubstituted or substituted linear, branched or cyclic chains of up to 15 carbon atoms that contain at least one heteroatom (e.g., nitrogen, oxygen or sulfur) in the chain. Linear heteroalkyl groups include, for example, CH$_2$CH$_2$OCH$_3$, CH$_2$CH$_2$N(CH$_3$)$_2$ and CH$_2$CH$_2$SCH$_3$. Branched groups include, for example, CH$_2$CH(OCH$_3$)CH$_3$, CH$_2$CH(N(CH$_3$)$_2$)CH$_3$ and CH$_2$CH (OCH$_3$)CH$_3$. Cyclic heteroalkyl groups include, for example, CH(CH$_2$CH$_2$)$_2$O, CH(CH$_2$CH$_2$)$_2$NCH$_3$ and CH(CH$_2$CH$_2$)$_2$S. Heteroalkyl groups can be substituted with one or more substituents. Nonlimiting examples of such substituents include NO$_2$, ONO$_2$, F, Cl, Br, I, OH, OCH$_3$, CO$_2$H, CO$_2$CH$_3$, CN, aryl and heteroaryl. Where "heteroalkyl" is used in a context such as "heteroalkyl-ONO$_2$," it refers to a heteroalkyl group that is substituted with an ONO$_2$ moiety. Where "heteroalkyl" is used in a context such as "C(O)heteroalkyl-NO$_2$," it refers to an alkyl group that is connected to a carbonyl group at one position and that is substituted with a ONO$_2$ moiety.

The term "Halo" refers to F, Cl, Br or I.

The term "Aryl" refers to an unsubstituted or substituted aromatic, carbocyclic group. Aryl groups are either single ring or multiple condensed ring compounds. A phenyl group, for example, is a single ring, aryl group. An aryl group with multiple condensed rings is exemplified by a naphthyl group. Aryl groups can be substituted with one or more substituents. Nonlimiting examples of such substituents include NO$_2$, ONO$_2$, F, Cl, Br, 1, OH, OCH$_3$, CO$_2$H, CO$_2$CH$_3$, CN, aryl and heteroaryl.

The term "Heteroaryl" refers an unsubstituted or substituted aromatic group having at least one heteroatom (e.g., nitrogen, oxygen or sulfur) in the aromatic ring. Heteroaryl groups are either single ring or multiple condensed ring compounds. Single ring beteroaryl groups having at least one nitrogen include, for example, tetrazoyl, pyrrolyl, pyridyl, pyridazinyl, indolyl, quinolyl, imidazolyl, iso-quinolyl, pyrazolyl, pyrazinyl, pyrimidinyl and pyridazinonyl. A furyl group, for example is a single ring heteroaryl group containing one oxygen atom. A condensed ring heteroaryl group containing one oxygen atom is exemplified by a benzofuranyl group. Thienyl, for example, is a single ring heteroaryl group containing one sulfur atom. A condensed ring heteroaryl group containing one sulfur atom is exemplified by benzothienyl. In certain cases, heteroaryl groups contain more than one kind of heteroatom in the same ring. Examples of such groups include furazanyl, oxazolyl, isoxazolyl; thiazolyl and phenothiazinyl. Heteroaryl groups can be substituted with one or more substituents. Nonlimiting examples of such substituents include $NO_2$, $ONO_2$, F, Cl, Br, I, OH, $OCH_3$, $CO_2H$, $CO_2CH_3$, CN, aryl and heteroaryl.

The compounds of the present invention are aminoadamantane derivatives. The aminoadamantane derivatives are of the following formula:

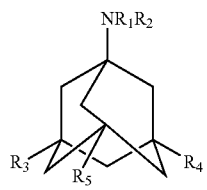

The groups $R_1$, $R_2$, $R_3$, $R_4$ and $R_5$ of the formula are independently defined. $R_1$ is H, alkyl, heteroalkyl, aryl, heteroaryl, $C(O)OR_6$ or $C(O)R_6$. $R_2$ is H, alkyl, heteroalkyl, aryl, heteroaryl, $C(O)OR_6$ or $C(O)R_6$. $R_3$ is H, alkyl, heteroalkyl, aryl or heteroaryl. $R_4$ is H, alkyl, heteroalkyl, aryl or heteroaryl. $R_5$ is $OR_7$, alkyl-$OR_7$ or heteroalkyl-$OR_7$. $R_6$ is alkyl, heteroalkyl, aryl or heteroaryl. $R_7$ is $NO_2$, $C(O)R_6$, $C(O)$alkyl-$ONO_2$ or $C(O)$heteroalkyl-$ONO_2$. The following substituents are preferred: $R_1$ and $R_2$ are H; $R_3$ and $R_4$ are H or alkyl; and, $R_7$ is $NO_2$ or $C(O)$alkyl-$ONO_2$.

Preferably, $R_1$ is H and $R_2$ is H, C(O)O-alkyl or C(O)O-aryl. Where $R_2$ is C(O)O-alkyl, it is preferred that the alkyl group is methyl, ethyl, n-propyl, iso-propyl, n-butyl, sec-butyl, tert-butyl or benzyl. Where $R_2$ is C(O)O-aryl, it is preferred that the aryl group is phenyl or a substituted phenyl. More preferably, $R_1$ and $R_2$ are both H.

Preferably, both $R_3$ and $R_4$ are H or linear alkyl groups. $R_3$ and $R_4$ can be the same or different. Where $R_3$ and $R_4$ are both alkyl groups, it is preferred that the groups are methyl, ethyl, n-propyl, n-butyl, sec-butyl, tert-butyl or benzyl.

Preferably, $R_5$ is $ONO_2$, O-alkyl-$ONO_2$ or OC(O)-alkyl-$ONO_2$. Where $R_5$ is O-alkyl-$ONO_2$, it is preferred that the alkyl group be $CH_2$, $CH_2CH_2$ or $CH_2CH_2CH_2$. Where $R_5$ is OC(O)-alkyl-$ONO_2$, it is preferred that the alkyl group be $CH_2$, $CH_2CH_2$, $CH_2CH_2CH_2$ or $CH_2CH_2CH_2$. More preferably, $R_5$ is $ONO_2$.

The aminoadamantane derivatives of the present invention are synthesized starting from a haloadamantane derivative. The haloadamantane derivative is treated with acid and a nitrile to form an amidoadamantane derivative. Treatment of the amidoadamantane derivative with an acid and second reagent provides a functionalized amidoadamantane derivative.

In certain cases, the second reagent used to form the functionalized amidoadamantane derivative is water. The compound formed in this case is an amido alcohol. The amido alcohol is either nitrated to provide an amido nitrate derivative or hydrolyzed to provide an amino alcohol derivative. Where an amino alcohol is formed, a variety of different steps can be used to make other aminoadamantane derivatives, including the following nonlimiting examples:

1) protection of the amine group, followed by nitration of the alcohol group and deprotection of the amine group to provide an amino nitrate derivative; 2) protection of the amine group, followed by esterification of the alcohol group and deprotection of the amine group to provide an amino ester derivative; and, 3) protection of the amine group, followed by esterification to with a halogenated acid chloride and nucleophilic displacement to provide an carbamate nitrate-ester derivative.

In other cases, the second reagent used to form the functionalized amidoadamantane derivative is formic acid. The compound formed in this case is an amido acid. The amido acid is subjected to conditions that form an amido alkanol. The amido alkanol is either nitrated to provide an amido alkane nitrate derivative or deprotected to provide an amino alkanol derivative. Where an amino alkanol derivative is formed, the amine group is protected to form an amido alkanol derivative, which is subsequently nitrated to provide an amido alkane-nitrate derivative. Deprotection of the amido group affords an amino alkane-nitrate derivative.

FIG. 1 shows the synthesis of an amido nitrate derivative. Compound 1, a dimethyl-bromo-adamantane, was treated with sulfuric acid and acetonitrile to afford the dimethyl amido compound 2. Amide 2 was reacted with sulfuric acid and water, providing amido alcohol 3, which was nitrated using nitric acid and acetic anhydride to form compound 8.

FIG. 1 also shows the synthesis of an amino nitrate derivative. Compound 3 was deprotected with sodium hydroxide, affording amino alcohol 4. The amine group of compound 4 was protected with $(BOC)_2O$ to form the carbamate alcohol 5. Carbamate 5 was nitrated using nitric acid and acetic anhydride, providing nitrate 6, which was deprotected upon treatment with hydrochloric acid to form amino nitrate hydrochloride salt 7.

Figure 2:
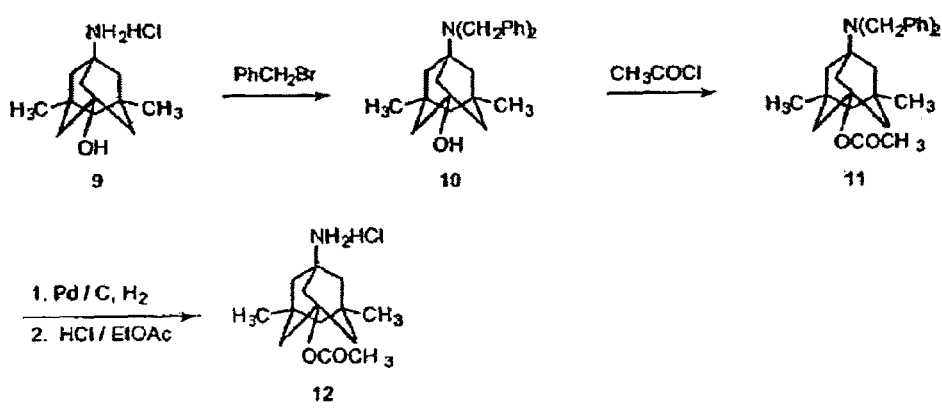
FIG. 2 shows the synthesis of an adamantane ester derivative.

FIG. 2 shows the synthesis of an amino ester derivative. Amino alcohol 9 was alkylated with two equivalents of benzyl bromide to afford protected amino alcohol 10. Compound 10 was acetylated, yielding ester 11. Ester 11 was subjected to hydrogenation and then acidified to provide the amino alcohol hydrochloride salt 12.

Figure 3:
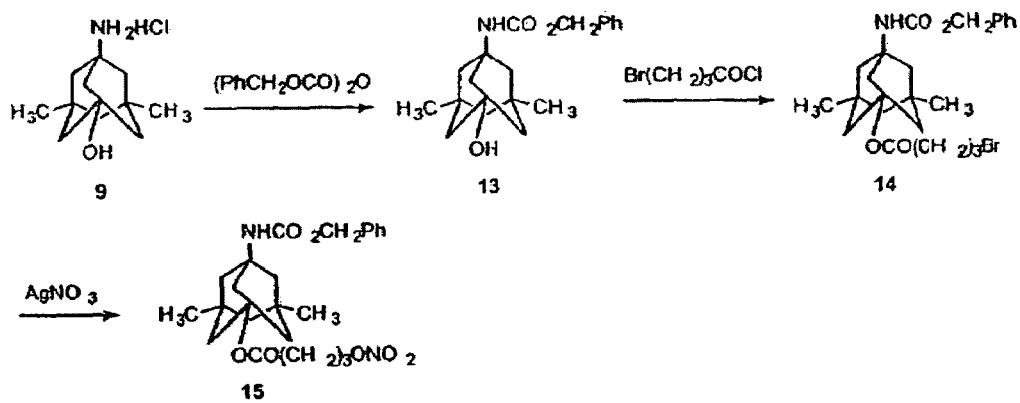
FIG. 3 shows the synthesis of halo and nitrate substituted adamantane ester derivatives.

FIG. 3 shows the synthesis of a carbamate nitrate-ester derivative. Amino alcohol 9 was protected upon treatment with $(PhCH_2OCO)_2O$, yielding carbamate 13. Carbamate 13 was esterified using a haloalkyl acid chloride to provide compound 14, which was subjected to nucleophilic displacement with $AgNO_3$, affording carbamate nitrate-ester 15.

Figure 4:
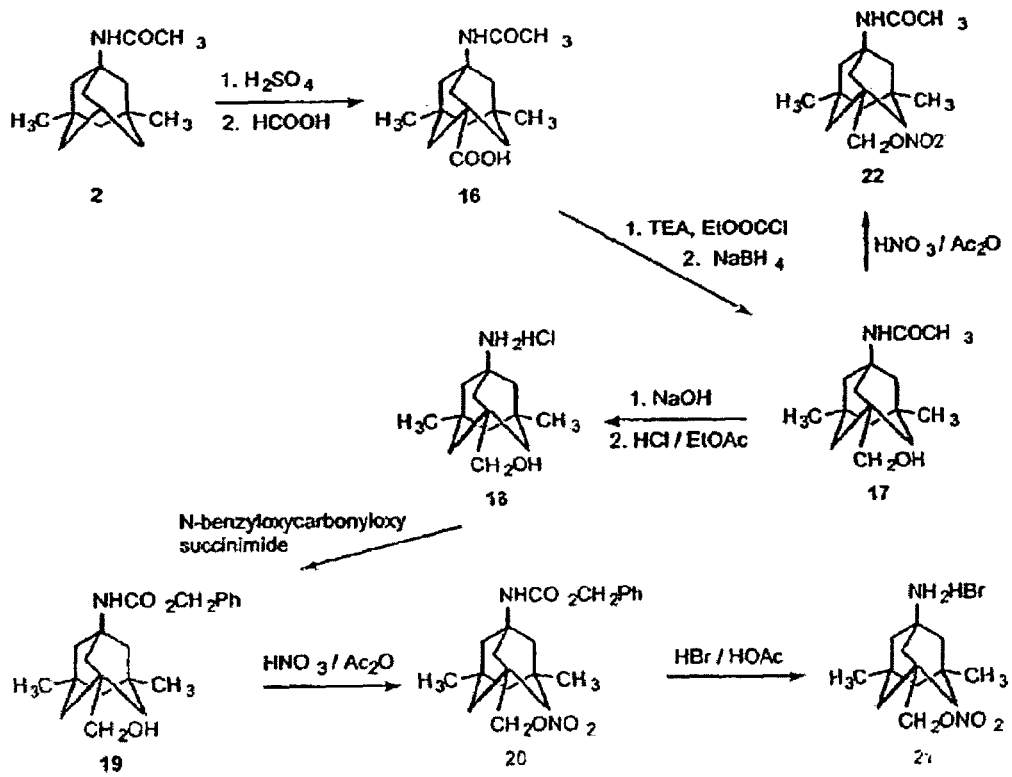
FIG. 4 shows the synthesis of an alkyl-ONO$_2$ derivative of adamantane.

FIG. 4 shows the synthesis of an amido alkyl-nitrate derivative. Amide 2 was reacted with sulfuric acid and formic acid to form amido acid 16. Treatment of compound 16 with triethyl amine and ethyl chloroformate, providing a mixed anhydride, followed by reduction with sodium borohydride yielded amido alkanol 17. Nitration of 17 using nitric acid and acetic anhydride afforded amido alkyl-nitrate 22.

FIG. 4 also shows the synthesis of an amino alkyl-nitrate derivative. Amido alkanol 17 was deprotected with sodium hydroxide and acidified with hydrochloric acid to provide 18. The amine group of compound 18 was protected upon reaction with N-benzyloxycarbonyloxysuccinimide, forming carbamate 19, and subsequently nitrated using nitric acid and acetic anhydride to yield carbamate alkyl-nitrate 20. The carbamate of compound 20 was removed with hydrobromic acid and acetic acid, providing amino alkyl-nitrate 21.

There are a number of compounds that are preferable intermediates for the synthesis of either amido or amino alkyl-nitrate derivatives. Such compounds include amido acid 16, amido alkanol 17 and amino alcohol hydrochloride salt 18.

The compounds and compositions of the present invention can be used to treat a number of disease states. Examples of neurological disorders arising from trauma, ischemic or hypoxic conditions that can be treated include stroke, hypoglycemia, cerebral schemia, cardiac arrest, spinal cord trauma, head trauma, perinatal hypoxia, cardiac arrest and hypoglycemic neuronal damage. Neurodegenerative disorders such as epilepsy, Alzheimer's disease, Huntington's disease, Parkinsonism, and amyotrophic lateral sclerosis can also be treated. Other diseases or disorders that can be ameliorated through administration of the compounds and compositions include, without limitation, the following: convulsion, pain, depression, anxiety, schizophrenia, muscle spasms, migraine headaches, urinary incontinence, nicotine withdrawal, opiate tolerance and withdrawal, emesis, brain edema, tardive dyskinesia, AIDS-induced dementia, ocular damage, retinopathy, cognitive disorders, and neuronal injury associated with HIV-infection such as dysfunction in cognition, movement and sensation.

The aminoadamantane derivatives of the present invention can be administered to a patient in the form of a pharmaceutically acceptable salt or in a pharmaceutical composition. A compound that is administered in a pharmaceutical composition is mixed with a suitable carrier or excipient such that a therapeutically effective amount is present in the composition. The term "therapeutically effective amount" refers to an amount of the aminoadamantane derivative that is necessary to achieve a desired endpoint (e.g., decreasing neuronal damage as the result of a stroke).

A variety of preparations can be used to formulate pharmaceutical compositions containing the aminoadamantane derivatives, including solid, semi solid, liquid and gaseous forms. *Remington's Pharmaceutical Sciences*, Mack Publishing Company (1995) Philadelphia, Pa., 19th ed. Tablets, capsules, pills, powders, granules, dragees, gels, slurries, ointments, solutions suppositories, injections, inhalants and aerosols are examples of such formulations. The formulations can be administered in either a local or systemic manner or in a depot or sustained release fashion. Administration of the composition can be performed in a variety of ways. Among others, oral, buccal, rectal, parenteral, intraperitoneal, intradermal, transdermal and intratracheal means can be used.

Where the aminoadamantane derivative is given by injection, it can be formulated by dissolving, suspending or emulsifying it in an aqueous or nonaqueous solvent. Vegetable or similar oils, synthetic aliphatic acid glycerides, esters of higher aliphatic acids and propylene glycol are examples of nonaqueous solvents. The compound is preferably formulated in aqueous solutions such as Hank's solution, Ringer's solution or physiological saline buffer.

Where the aminoadamantane derivative is given orally, it can be formulated through combination with pharmaceutically acceptable carriers that are well known in the art. The carriers enable the compound to be formulated, for example, as a tablet, pill, suspension, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxypropylmethyl-cellulose, sodium carboxymethylcellulose and polyvinylpyrrolidone (PVP).

The aminoadamantane derivative of the present invention can also be delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Pharmaceutical compositions of the present invention contain a therapeutically effective amount of the aminoadamantane derivative. The amount of the compound will depend on the patient being treated. The patient's weight, severity of illness, manner of administration and judgment of the prescribing physician should be taken into account in deciding the proper amount. The determination of a therapeutically effective amount of an aminoadamantane derivative is well within the capabilities of one with skill in the art.

Although a therapeutically effective amount of an aminoadamantane derivative will vary according to the patient being treated, suitable doses will typically include between about 0.1 mg and 1000 mg of the compound. Preferably, a dose contains between about 0.1 mg and 500 mg of the compound. More preferably, a dose contains between about 0.1 mg and 250 mg of the compound.

In some cases, it may be necessary to use dosages outside of the stated ranges to treat a patient. Those cases will be apparent to the prescribing physician. Where it is necessary, a physician will also know how and when to interrupt, adjust or terminate treatment in conjunction with a response of a particular patient.

The following examples are provided to illustrate, not limit, the present invention.

EXAMPLE 1

Synthesis of 1-acetamido-3,5 dimethyl-7-hydroxyadamantane (3)

Fuming $H_2SO_4$ (3 mL) was added to 1-acetamido-3,5-dimethyladamantane (0.2 g) at 0° C. under nitrogen and the reaction mixture was stirred at 0° C. for 1 h. The reaction mixture was poured onto ice (10 g) and the product was extracted with ether (10 mL×4). The combined ether solution was washed with brine (10 mL) and water (10 mL). The solution was dried using sodium sulfate. The solvent was removed in vacuo and, after crystallization on standing, 70 mg of white product was obtained. Pure product was obtained by recrystallization in ether. $^1H$ NMR (DMSO-$d_6$, ppm): 7.30 (brs, 1 H, NH), 4.37 (brs, 1H, OH), 1.72 (s, 3H, $COCH_3$), 1.65 (s, 2H), 1.47 (s, 4H), 1.24-1.14 (dd, 4H, J=11.2, 23.9 Hz), 0.99 (s, 2H), 0.82 (s, 6H, 2×$CH_3$). m.p. 194-195° C. Anal. ($C_{14}H_{23}NO_2$), C. H. N.

EXAMPLE 2

Synthesis of 1-amino-3,5-dimethyl-7-hydroxyadamantane hydrochloride (4)

1-Acetamido-3,5-dimethyl-7-hydroxyadamantane (0.4 g) and NaOH (1.1 g) were added to diethylene glycol (7 mL) and the reaction mixture was heated to 175° C. for 15 h. After cooling to room temperature, ice (10 g) was added and the product was extracted with ether (10 mL×4). The combined ether solution was washed with brine (10 mL) and water (10 mL). The solution was dried using sodium sulfate. The solvent was removed in vacuo and, after crystallization on standing, 250 mg of white product was obtained. HCl in ethyl acetate was added to convert the free base to HCl salt. $^1$H NMR (DMSO-$d_6$, ppm): 8.12 (brs, 2H, NH), 4.72 (brs, 1H, OH), 1.58 (s, 2H), 1.40-1.31 (dd, 4H, J=12.3, 21.6 Hz), 1.23 (s, 4H), 1.08-0.98 (dd, 2H, J=12.6, 23.3 Hz), 0.88 (s, 6H, 2×CH$_3$). m. p. 281-282° C. Anal. ($C_{12}H_{22}NOCl+0.5 H_2O$), C. H. N.

EXAMPLE 3

Synthesis of 1-tert-butylcarbamate-3,5-dimethyl-7-hydroxy-adamantane (5)

1-Amino-3,5-dimethyl-7-hydroxyadamantane (100 mg) was dissolved in tetrahydrofuran (2 mL). Triethylamine (180 mL), di-tert-butyl dicarbonate (336 mg) and dimethylaminopyridine (2 mg) were added sequentially. The reaction mixture was stirred at room temperature for 3 h and then 0.5 N NaOH (2 mL) was added. The reaction mixture was stirred overnight. Triethylamine was removed in vacuo and ether was added. The ether solution was washed with 0.1 N HCl and brine. The solution was dried using sodium sulfate. Solvent was removed in vacuo and 60 mg of product was obtained after crystallization on standing in ether. $^1$H NMR (DMSO-$d_6$, ppm): 6.35 (brs, 1H, NH), 4.35 (brs, 1H, OH), 1.59 (s, 2H), 1.40 (s, 4H), 1.35 (s, 9H, 3×CH$_3$), 1.22-1.13 (dd, 4H, 3=11.1, 20.6 Hz), 0.99 (s, 2H), 0.82 (s, 6H, 2×CH$_3$).

EXAMPLE 4

Synthesis of 1-tert-butylcarbamate-3,5-dimethyl-7-nitrate-adamantane (6)

A cooled (0° C.) acetyl nitrate (0.08 mL, from a mixture of fuming HNO$_3$ and acetic anhydride (1:1.5/v:v) was added to a dichloromethane (1 mL) solution of 1-tert-butylcarbamate-3,5-dimethyl-7-hydroxyadamantane (40 mg) at 0° C. under nitrogen and the reaction mixture was stirred at 0° C. for 15 minutes. 1 N sodium hydrogen carbonate solution (5 mL) was added and the product was extracted with dichloromethane (10 mL). The dichloromethane solution was washed with water (10 mL×3). The solution was dried using sodium sulfate. The solvent was removed in vacuo to afford an oily product (30 mg). $^1$H NMR (DMSO-$d_6$, ppm): 6.66 (brs, 1H, NH), 2.14 (s, 2H), 1.70 (s, 2H), 1.69 (s, 2H), 1.63-1.60 (d, 2H, J=12.3 Hz), 1.46-1.43 (d, 2H, J=12.2 Hz), 1.36 (s, 9H, 3×CH$_3$), 1.17-1.08 (dd, 2H, J=11.4, 22.6 Hz), 0.91 (s, 6H, 2×CH$_3$). High resolution MS Calcd for $C_{17}H_{28}N_2O_5Na$ (MS+Na): 363.1895. Found 363.1908.

EXAMPLE 5

Synthesis of 1-amino-3,5-dimethyl-7-nitrateadamantane hydrochloride (7)

3 N HCl in ethyl acetate (0.5 mL) was added to 1-tert-butylcarbamate-3,5-dimethyl-7-nitrateadamantane (40 mg). The reaction mixture was stirred at room temperature for 30 minutes. The precipitate was filtered and the product was washed with ether. A pure white product was obtained (35 mg). $^1$H NMR (DMSO-$d_6$, ppm): 8.36 (brs, 2 H, NH), 2.15 (s, 2H), 1.69 (s, 4H), 1.57-1.44 (dd, 4H, J=12.2, 32.8 Hz), 1.26-1.0 (dd, 2 H, J=12.0, 44.3 Hz), 0.96 (s, 6H, 2×CH$_3$). m. p. 225-226° C. MS (MS+H$^+$): 241. Anal. ($C_{12}H_{21}N_2O_3Cl$), C. H. N.

EXAMPLE 6

Synthesis of 1-acetamido-3,5-dimethyl-7-nitrateadamantane (8)

To acetic anhydride (0.3 mL) at 0° C. under nitrogen was added fuming HNO$_3$ (0.2 mL). After stirring for 5 minutes at 0° C., 1-acetamido-3,5-dimethyl-7-hydroxyadamantane (50 mg) was added and the reaction mixture was stirred at 0° C. for 1 h. The reaction mixture was poured into cold (0° C.) 1 N sodium hydrogen carbonate solution (20 mL) and the product was extracted with ether (10 mL). The ether solution was washed with water (10 mL×3). The solution was dried using sodium sulfate. The solvent was removed in vacuo and 31 mg of product was obtained. $^1$H NMR (DMSO-$d_6$, ppm): 7.52 (brs, 1H, NH), 2.23 (s, 2H), 1.73-1.66 (m, 9H, COCH$_3$, 3×CH$_2$), 1.51-1.47 (m, 2H), 1.15-1.13 (m, 2H), 0.92 (s, 6H, 2×CH$_3$). m. p. 152-153° C. Anal. ($C_{14}H_{22}N_2O_4$), C. H. N.

EXAMPLE 7

Synthesis of 1,1-dibenzylamino-3,5-dimethyl-7-hydroxy-adamantane (10)

To a solution of 1-amino-3,5-dimethyl-7-hydroxyadamantane hydrochloride (100 mg) in DMF (2 mL) was added benzyl bromide (0.16 mL) and sodium carbonate (200 mg). The reaction mixture was stirred overnight. The product was extracted with dichloromethane (10 mL) and washed with water (20 mL×2). The organic phase was dried using sodium sulfate and the solvent was removed in vacuo. The product was purified by flash column chromatography eluting with ethyl acetate and hexane (1/2, v/v) to afford 124 mg of white solid (76% yield). $^1$H NMR (DMSO-$d_6$, ppm): 7.31-7.04 (m, 10H, 2×C$_6$H$_5$), 4.32 (1H, OH), 3.71 (s, 4H, 2×C$_6$H$_5$CH$_2$), 1.44 (s, 2H), 1.35-1.27 (m, 4H), 1.22-1.13 (dd, 4H, J=11.8, 21.2 Hz), 0.97 (s, 2H), 0.81 (s, 6H, 2×CH$_3$).

EXAMPLE 8

Synthesis of 1-amino-3,5-dimethyl-7-acetoxyadamantane hydrochloride (12)

To a solution of 1,1-dibenzylamino-3,5-dimethyl-7-hydroxyadamantane (50 mg) in DMF (0.4 mL) was added dichloromethane (2 mL). Acetyl chloride (1 mL) was added at 0° C. under nitrogen and the reaction mixture was stirred overnight. Saturated sodium carbonate solution (5 mL) was added. The product was extracted with dichloromethane (10 mL) and washed with water (20 mL×2). The organic phase was dried using sodium sulfate and the solvent was removed in vacuo. Without further purification, the product was dissolved in methanol (10 mL). Pd/C (10%, 10 mg) was added and the reaction mixture was hydrogenated at a pressure of 40 LB/inch$^2$ overnight. The mixture was filtered and solvent was removed. HCl in ethyl acetate was added and the precipitate was filtered and the solid was washed with hexane to afford 15 mg of product after drying in air. $^1$H NMR (DMSO-$d_6$, ppm): 8.30 (brs, 2H, NH$_2$), 2.09 (s, 2H), 1.93 (s, 3 H, COCH$_3$), 1.72-1.63 (dd, 4H, J=12.6, 21.4 Hz), 1.50-1.39 (dd, 4H, J=11.7, 29.6 Hz), 1.18-1.05 (dd, 2H, J=14.1, 36.5 Hz), 0.93 (s, 6H, 2×CH$_3$).

EXAMPLE 9

Synthesis of 1-(benzyloxycarbonyl)amino-3,5-dimethyl-7-hydroxyadamantane (13)

To a solution of 1-amino-3,5-dimethyl-7-hydroxyadamantane hydrochloride (570 mg) in DMF (5 mL) and water (0.3 mL) was added dibenzyl dicarbonate (1.41 g) and sodium carbonate (1.3 g). The reaction mixture was stirred overnight. The product was extracted with t-butyl methyl ether (500 mL) and washed with water (400 mL×2). The organic phase was dried using sodium sulfate and the solvent was removed in vacuo. The product was purified by flash column chromatography eluting with ethyl acetate and hexane (1/3, v/v) to afford 701 mg of white solid. $^1$H NMR (DMSO-d$_6$, ppm): 7.35-7.28 (m, 5H, C$_6$H$_5$), 6.96 (brs, 1H, NH), 4.94 (s, 2H, OCH$_2$), 4.41 (1H, OH), 1.62 (s, 2H), 1.43 (s, 4H), 1.24-1.14 (dd, 4H, J=11.5, 22.0 Hz), 0.97 (s, 2H), 0.83 (s, 6H, 2×CH$_3$).

EXAMPLE 10

Synthesis of 1-(benzyloxycarbonyl)amino-3,5-dimethyl-7-(3-bromopropylcarbonyloxy)adamantane (14)

To a solution of 1-(benzyloxy-carbonyl)amino-3,5-dimethyl-7-hydroxyadamantane (100 mg) in DMF (0.4 mL) was added 4-bromobutyryl chloride (0.3 mL). The reaction mixture was stirred for 2 h at room temperature. The mixture was purified by thin layer chromatography eluting with ethyl acetate and hexane (1/2, v/v) to afford an oily product. $^1$H NMR (DMSO-d$_6$, ppm): 7.38-7.29 (m, 5H, C$_6$H$_5$), 7.12 (brs, 1H, NH), 4.95 (s, 2H, OCH$_2$), 3.53-3.49 (t, 2H, J=6.6 Hz, COCH$_2$), 2.36-2.32 (t, 2H, J=7.7 Hz, CH$_2$Br), 2.10 (s, 2H), 2.00-1.96 (m, 2H, CH$_2$CH$_2$CH$_2$), 1.66 (s, 4H), 1.59-1.41 (dd, 4H, J=11.5, 51.7 Hz), 1.08-1.07 (d, 2H, J=3.8 Hz), 0.87 (s, 6H, 2×CH$_3$).

EXAMPLE 11

Synthesis of 1-(benzyloxycarbonyl)amino-3,5-dimethyl-7-(3-nitratepropylcarbonyloxy)adamantane (15)

To a solution of 1-(benzyloxy carbonyl)amino-3,5-dimethyl-7-(3-bromopropylcarbonyloxy)adamantane in acetonitrile was added a solution of silver nitrate in acetonitrile and the reaction mixture was stirred overnight in dark. The product was extracted with t-butyl methyl ether and the solution was washed with water. The organic phase was dried using sodium sulfate and solvent was removed to afford the nitrate compound.

EXAMPLE 12

1-Acetamido-3,5-dimethyl-7-carboxylic acidadamantane (16)

To fuming H$_2$SO$_4$ (15 mL) in a flask cooled to 0° C. 1-acetamido-3,5-dimethyl-adamantane (1.0 g) was added slowly over a period of 1 h. The reaction mixture was stirred for 2 h at 0° C. Formic acid (3 mL) was then added dropwise over 1 h. The solution was stirred at 0° C. for another 2 h. The reaction mixture was poured onto ice (100 g) slowly with vigorous stirring. The precipitate formed was filtered and washed with water to give a pure white solid (0.37 g). m. p. 261-262° C.

EXAMPLE 13

1-Acetamido-3,5-dimethyl-7-hydroxymethyladamantane (17)

Triethylamine (0.80 mL) and ethyl chloroformate (0.80 mL) were added sequentially into a suspension of 1-acetamido-3,5-dimethyl-7-carboxylic acid-adamantane (2.0 g) in THF at 0° C. The reaction mixture was stirred for 4 h at room temperature. The white precipitate formed was then filtered and washed with THF. NaBH$_4$ (2.40 g) was added to the filtrate. Water (2 mL) was added dropwise to the solution over a period of 1 h followed by addition of more water (50 mL). The organic solvent was removed under reduced pressure and the remaining aqueous solution was extracted with ethyl acetate (100 mL×3). The combined organic extracts were washed with 0.5 N HCl twice, water, and brine. Solvent was removed in vacuo and the product was crystallized using a solution of ethyl acetate and hexane (1/4, v/v) to give a white solid (700 mg). $^1$H NMR (DMSO-d$_6$, ppm): 7.28 (s, 1H, NH), 4.33 (t, 1H, OH, J=5.7 Hz), 3.02 (d, 2H, CH$_2$OH, J=5.7 Hz), 1.71 (s, 3H, COCH$_3$), 1.49 (s, 6H), 1.07-0.97 (m, 6H), 0.96 (s, 6H). m. p. 152-153° C. Anal. (C$_{15}$H$_{25}$NO$_2$), C. H. N.

EXAMPLE 14

1-Amino-3,5-dimethyl-7-hydroxymethyladamantane hydrochloride (18)

1-Acetamido-3,5-dimethyl-7-hydroxymethyladamantane (200 mg) and NaOH (540 mg) were added to diethylene glycol (4 mL) and the reaction mixture was heated to 175° C. under nitrogen for 15 h. After cooling to room temperature, ice (5 g) was added and the product was extracted with ethyl acetate (10 mL×6). The combined extract was washed with water (10 mL) and brine (10 mL), and dried using sodium sulfate. Solvent was removed in vacuo. HCl in ethyl acetate was added to convert the free base to HCl salt and 102 mg of product was obtained. $^1$H NMR (DMSO-d$_6$, ppm): 8.19 (brs, 2H), 4.54-4.51 (t, 1 H, OH, J=5.0 Hz), 3.07-3.05 (d, 2H, OCH$_2$, J=4.6 Hz), 1.42-1.40 (m, 6H), 1.01-0.99 (m, 6H), 0.86 (s, 6H). Anal. (C$_{13}$H$_{24}$NOCl+0.4 HCl), C. H. N.

EXAMPLE 15

1-(benzyloxycarbonyl)amino-3,5-dimethyl-7-hydroxymethyl adamantane (19)

To a solution of 1-amino-3,5-dimethyl-7-hydroxymethyl adamantane (60 mg) in THF (3 mL) was added N-(benzyloxycarbonyloxy)-succinimide (74 mg) and the mixture was stirred at room temperature overnight. THF was removed and the residue was dissolved in ethyl acetate. The solution was washed with water and brine. The product was purified by thin layer chromatography eluting with ethyl acetate and hexane (1:4, v/v) to give a white solid (80 mg). $^1$H NMR (DMSO-d$_6$, ppm): 7.33 (m, 5H, C$_6$H$_5$), 6.89 (brs, 1H, NH), 4.94 (s, 2H, OCH$_2$), 4.32 (t, 1H, OH, J=5.7 Hz), 3.04 (d, 2H, CH$_2$OH, J=5.7 Hz), 1.46 (dd, 6H), 1.04 (dd, 6H), 0.84 (s, 6H, 2×CH$_3$).

EXAMPLE 16

1-(benzyloxycarbonyl)amino-3,5-dimethyl-7-nitratemethyl-adamantane (20)

To a solution of 1-(benzyloxycarbonyl)amino-3,5-dimethyl-7-hydroxymethyladamantane (60 mg) in dichloromethane (3 mL) was added a cooled (0° C.) acetyl nitrate (1 mL, from a mixture of fuming $HNO_3$ and $Ac_2O$ (2:3/v:v). The reaction mixture was stirred at 0° C. for 15 minutes. A sodium bicarbonate solution (1 N, 5 mL) was added and the product was extracted with dichloromethane. The extract was washed with water (10 mL×3). Solvent was removed in vacuo and the residue was purified by thin layer chromatography eluting with ethyl acetate and hexane (1:2, v/v) to give an oily product (40 mg). $^1H$ NMR (DMSO-$d_6$, ppm): 7.33 (m, 5H, $C_6H_5$), 7.02 (brs, 1H, NH), 4.95 (s, 2H, $OCH_2$), 424 (s, 2H, $OCH_2$), 1.60 (s, 2H), 1.55 (d, 2H), 1.44 (d, 2H), 1.12 (m, 6H), 0.83 (s, 6H, 2×$CH_3$).

EXAMPLE 17

1-Amino-3,5-dimethyl-7-nitratemethyladamantane hydrobromide (21)

1-(benzyloxycarbonyl)amino-3,5-dimethyl-7-nitratemethyl-adamantane (17 mg) was dissolved in HBr/acetic acid (1 mL) and the solution was stirred at room temperature for 2 h. The reaction mixture was concentrated in vacuo to give a white solid which was washed with ether to afford the target product (10 mg). $^1H$ NMR (DMSO-$d_6$, ppm): 7.82 (brs, 3H), 4.30 (s, 2H, $OCH_2$), 1.50 (s, 2H), 1.39 (s, 4H), 1.19 (s, 4H), 1.12 (s, 2 H), 0.88 (s, 6H, 2×$CH_3$).

EXAMPLE 18

Synthesis of 1-acetamido-3,5-dimethyl-7-nitratemethyl-adamantane (22)

To acetic anhydride (0.3 mL) at 0° C. under nitrogen was added fuming $HNO_3$ (0.2 mL). After stirring for 5 minutes at 0° C., 1-acetamido-3,5-dimethyl-7-hydroxymethyladamantane (50 mg) was added and the reaction mixture was stirred at 0° C. for 1 h. The reaction mixture was poured into cold (0° C.) 1 N sodium hydrogen carbonate solution (20 mL) and the product was extracted with ether (10 mL). The ether solution was washed with water (10 mL×3). The solution was dried using sodium sulfate. The solvent was removed in vacuo and the product was crystallized in ether to afford the target product. $^1H$ NMR (DMSO-$d_6$, ppm): 7.38 (brs, 1H, NH), 4.23 (s, 2H, $OCH_2$), 1.72 (s, 3H, $COCH_3$), 1.64 (s, 2H), 1.59-1.56 (dd, 4H), 1.20-1.06 (m. 6H), 0.92 (s, 6H, 2×$CH_3$). m.p. 154-155 0° C. Anal. ($C_{15}H_{24}N_2O_4$), C. H. N.

EXAMPLE 19

In Vitro Protection of Neurons by Compound 7

Figure 5:
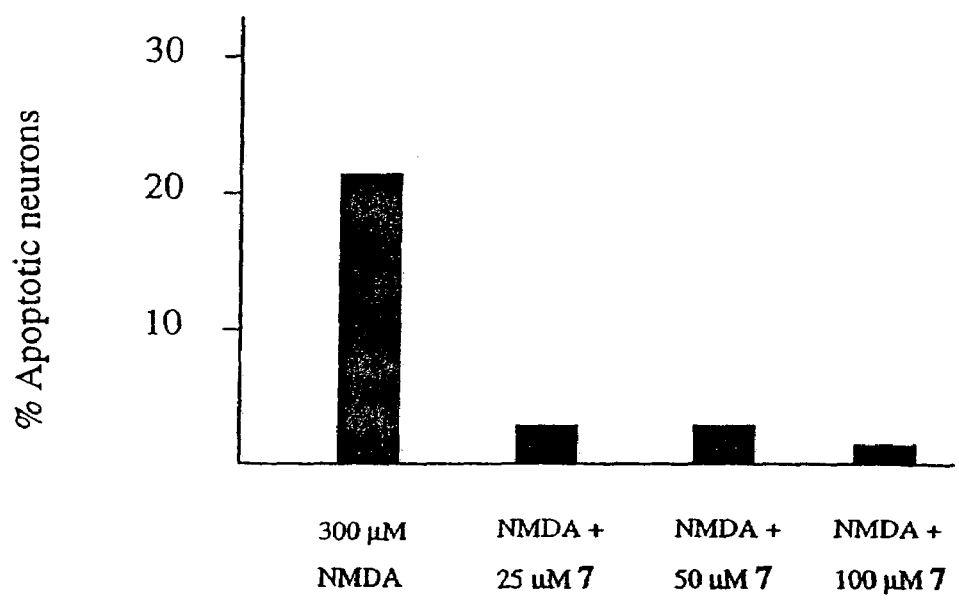
FIG. 5 shows the inhibition of NMDA induced apoptosis in cerebrocortical neurons by compound 7. Cerebrocortical cultures were exposed to 300 μM NMDA for 20 min with or without various concentrations of compound 7. The next day cultures were analyzed by neuronal apoptosis as described in Example 19. Neuronal apoptosis was largely prevented by compound 7 in a dose-dependent manner (P<0.001, n=3 cultures in each case).

An in vitro model of mild NMDA—induced damage leading to apoptosis of cerebrocortical neurons was used to demonstrate the protection of neurons by compound 7. Under these conditions (300 μM NMDA exposure for 20 min, followed by washout), neuronal apoptosis was monitored 24 hours later by propidium iodide uptake and morphology of fixed, permeabilized neurons, among other techniques (Bonfoco et al., Proc Natl Acad Sci USA (1995) 92: 7162). NMDA induced about 20% apoptosis of neurons, and that 25-100 μM compound 7 afforded protection from this damage ($p<0.001$, FIG. 5).

EXAMPLE 20

In Vivo Protection by Compound 7 in a Murine Cerebral Ischemia Model.

Figure 6:
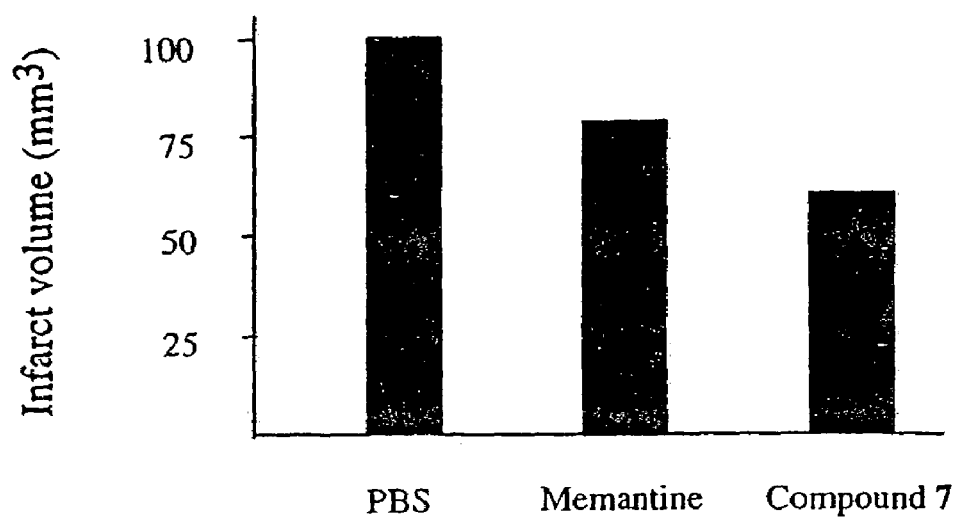
FIG. 6 shows that administration of compound 7 decreases cerebral damage after stroke in a murine cerebral ischemia model as compared to both a control and memantine (see Example 20). Use of the intraluminal suture method demonstrated (n=3 for each group) that compound 7 was effective in decreasing cerebral damage after stroke (P<0.03 from control: P<0.05 from memantine).

The intraluminal suture technique was used to produce a 2 hr occlusion of the middle cerebral artery (MCA), following the same protocol for focal cerebral ischemia/reperfusion as published previously (Chen, et al., Neuroscience (1998) 86: 1121). However, here C57B1/6 mice were used instead of rats. For memantine the loading dose was 20 mg/kg i.p. with a maintenance dose of 1 mg/kg/12 hours, as this had been previously shown to produce parenchymal levels of 1-10 μM memantine in the brain, which was shown to be neuroprotective (Chen, et al., Neuroscience (1998) 86: 1121). To produce a neuroprotective concentration of compound 7, the loading dose was 100 mg/kg i.p. and the maintenance dose was 40 mg/kg i.p. every 12 hr. In each case, drug or vehicle control was initially administered 2 hr after MCA occlusion. Compound 7 was more neuroprotective than memantine under this paradigm (FIG. 6). The animals were sacrificed and analyzed with TTC staining 48 hr after MCA occlusion (Chen, et al., Neuroscience (1998) 86: 1121).

EXAMPLE 21

Vasodilation by Compound 8 in a Rabbit Model

New Zealand white female rabbits weighing 3-4 kilograms were anesthetized with sodium pentobarbital, 13 milligram per kilogram. Descending thoracic aorta were isolated, the vessels were cleaned of adherent tissue and the endothelium was removed by a gentle rubbing with a cotton-tipped applicator inserted into the lumen. The vessels were cut into 5 millimeter rings and mounted on stirrups connected to transducers by which changes in isometric tension were recorded (model TO3C, Grass Instruments, Quincy, Mass.). Vessel rings were suspended in 20 mL of oxygenated Krebs buffer at 37° C. and sustained contractions were induced with 1 μM norepinephrine. The vessels were then relaxed in a dose-dependent fashion ($10^{-9}$ through $10^{-5}$ M compound 8). In some experiments vessels were pretreated with methylene blue or hemoglobin to block relaxations.

Figure 7:
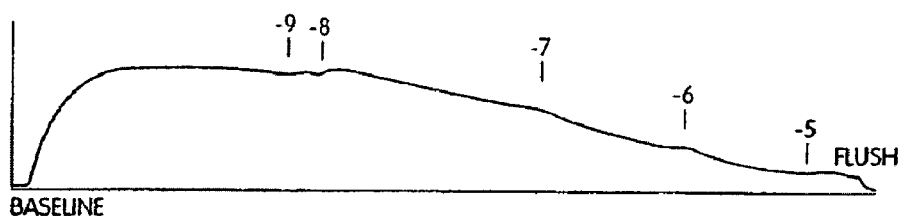
FIG. 7 shows that administration of compound 8 relaxes a precontracted aortic vessel in a dose-dependent fashion (see Example 21).
Figure 7:
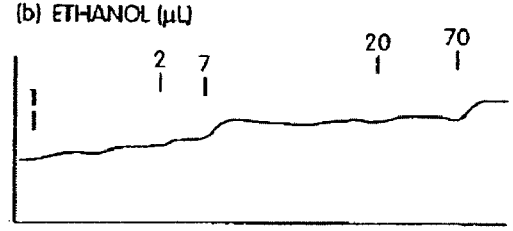
Figure 7:
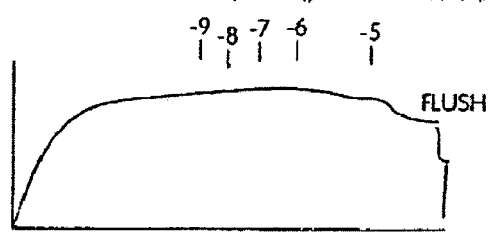
Figure 7:
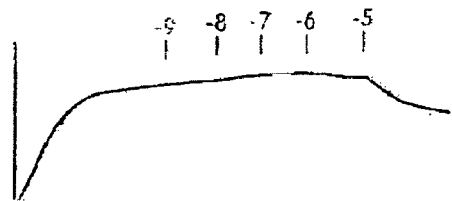

FIG. 7 shows relaxation of the precontracted aortic vessel in a dose-dependent fashion using compound 8. Relaxations were seen at $10^{-8}$ M and complete relaxation was achieved at $10^{-6}$ M (a). Relaxations were attenuated by methylene blue (c) and hemoglobin (d) indicating an NO-related effect. (b) is a control with solvent.

FIG. 8 shows site and specificity to derivatization of memantine. That is, compound 9 (a) and 10 (c) produced either no effect or slight contractions of blood vessels that were attributed to solvent (shown on right side). Compound 7 (b) produced modest relaxation at a 10 microM concentration.

These results demonstrate that compound 7 has vasodilator activity, in addition to NMDA-inhibitory and antiapoptic properties. Compound 7 thus acts through a unique mechanism of action that likely contributes to protective effects in models of stroke.

The scientific publications, patents or patent applications cited in the various sections of this document are herein incorporated-by-reference for all purposes.

What is claimed is:

1. A compound having the formula:

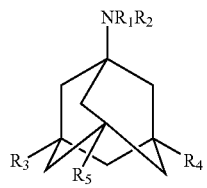

or a pharmaceutically acceptable salt thereof, wherein:
$R_1$ is H, alkyl, heteroalkyl, aryl, or heteroaryl;
$R_2$ is H, alkyl, heteroalkyl, aryl, or heteroaryl;
$R_3$ is H, alkyl, or heteroalkyl;
$R_4$ is H, alkly, or heteroalkyl;
$R_5$ is alkyl-$OR_7$; and
$R_7$ is $NO_2$.

2. The compound of claim 1, having the formula

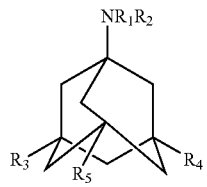

or a pharmaceutically acceptable salt thereof, wherein:
$R_1$ is H or alkyl;
$R_2$ is H or alkyl;
$R_3$ is alkyl;
$R_4$ is alkyl;
$R_5$ is alkyl-$OR_7$; and
$R_7$ is $NO_2$.

3. The compound of claim 1, wherein $R_1$ and $R_2$ are each H.

4. The compound of claim 1, wherein $R_3$ and $R_4$ are each methyl.

5. The compound of claim 1, wherein $R_5$ is $CH_2$-$OR_7$.

6. The compound of claim 1, wherein the pharmaceutically acceptable salt is an acid addition salt.

7. The compound of claim 1, wherein the pharmaceutically acceptable salt is a selected from a hydrochloride salt and a hydrobromide salt.

8. The compound of claim 7, wherein the pharmaceutically acceptable salt is a hydrobromide salt.

9. A composition comprising the compound of claim 1, and a carrier or excipient.

10. A pharmaceutical composition comprising the compound of claim 1, and a pharmaceutically acceptable carrier or excipient.

11. A compound having the formula:

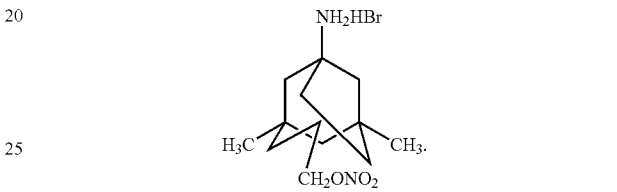

12. A composition comprising the compound of claim 11, and a carrier or excipient.

13. A pharmaceutical composition comprising the compound of claim 11, and a pharmaceutically acceptable carrier or excipient.

* * * * *

UNITED STATES PATENT AND TRADEMARK OFFICE
CERTIFICATE OF CORRECTION

PATENT NO. : 7,326,730 B2  
APPLICATION NO. : 11/283241  
DATED : February 5, 2008  
INVENTOR(S) : Yuqiang Wang et al.

It is certified that error appears in the above-identified patent and that said Letters Patent is hereby corrected as shown below:

Title Page, Item (75) Inventor name, "Jonathan S. Stemler" should read --Jonathan S. Stamler--.

Column 15, Line 15 Claim 1, that portion reading "alkly" should read --alkyl--.

Column 16, Line 8 Claim 7, that portion reading "salt is a selected from" should read --salt is selected from--.

Signed and Sealed this

Twenty-ninth Day of July, 2008

JON W. DUDAS  
*Director of the United States Patent and Trademark Office*